(12) United States Patent
Chan et al.

(10) Patent No.: US 12,245,866 B2
(45) Date of Patent: Mar. 11, 2025

(54) LABEL-FREE SPECTRAL PATHOLOGY FOR IN VIVO DIAGNOSIS

(71) Applicant: The Regents of the University of California, Oakland, CA (US)

(72) Inventors: James Chan, Davis, CA (US); Payam Saadai, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 315 days.

(21) Appl. No.: 17/775,231

(22) PCT Filed: Nov. 6, 2020

(86) PCT No.: PCT/US2020/059539
§ 371 (c)(1),
(2) Date: May 6, 2022

(87) PCT Pub. No.: WO2021/092489
PCT Pub. Date: May 14, 2021

(65) Prior Publication Data
US 2022/0386939 A1 Dec. 8, 2022

Related U.S. Application Data

(60) Provisional application No. 62/931,905, filed on Nov. 7, 2019.

(51) Int. Cl.
*A61B 5/00* (2006.01)
*A61B 1/31* (2006.01)
(Continued)

(52) U.S. Cl.
CPC .............. *A61B 5/4255* (2013.01); *A61B 1/31* (2013.01); *A61B 5/0071* (2013.01);
(Continued)

(58) Field of Classification Search
CPC ................................ A61B 5/0075; G01J 3/44
See application file for complete search history.

(56) References Cited

U.S. PATENT DOCUMENTS

2009/0040517 A1* 2/2009 Maier .................... G06V 20/69
702/19
2010/0130871 A1 5/2010 Frykman et al.
(Continued)

OTHER PUBLICATIONS

Faris Sinjab, Giovanna Sicilia, Dustin W. Shipp, Maria Marlow, and Ioan Notingher, "Label-Free Raman Hyperspectral Imaging of Single Cells Cultured on Polymer Substrates," Appl. Spectrosc. 71, 2595-2607 (2017) (Year: 2017).*
(Continued)

*Primary Examiner* — Joseph M Santos Rodriguez
*Assistant Examiner* — Tommy T Ly
(74) *Attorney, Agent, or Firm* — Foley & Lardner LLP

(57) ABSTRACT

A method for determining if a tissue is ganglionic is provided. The method comprises a) generating at least one hyperspectral Raman image of a tissue from a region of interest in a tissue suspected to contain ganglion cells that was optionally identified by a method comprising autofluorescence (AF) and Second Harmonic generation (SHG) imaging of the tissue; and b) analyzing any of the images for one or more of the following: i) optical excitation; ii) chemical information or emission spectra; or iii) AF, SHG, and/or Raman signatures, wherein the analysis provides indicators that the region of interest is either ganglionic or non-ganglionic. A system for analysis of in vivo tissue or ex vivo tissue samples including a multiphoton autofluorescence microscope, a Second Harmonic Generation microscope, and a hyperspectral Raman microscope in operative communication is also provided.

16 Claims, 14 Drawing Sheets

(51) Int. Cl.
*G01J 3/44* (2006.01)
*G01N 21/65* (2006.01)

(52) U.S. Cl.
CPC .......... *A61B 5/0075* (2013.01); *A61B 5/4029* (2013.01); *A61B 5/4893* (2013.01); *A61B 5/725* (2013.01); *G01J 3/44* (2013.01); *G01N 21/65* (2013.01)

(56) References Cited

U.S. PATENT DOCUMENTS

| | | | | |
|---|---|---|---|---|
| 2013/0057873 A1* | 3/2013 | Brown, III | ........... | A61B 5/0059 356/517 |
| 2014/0273207 A1 | 9/2014 | Chan et al. | | |
| 2014/0350379 A1* | 11/2014 | Verdooner | ............. | A61B 3/102 600/407 |
| 2019/0369025 A1* | 12/2019 | Yang | .................... | A61B 5/4547 |
| 2020/0088712 A1* | 3/2020 | Bosser | ................. | G01N 33/487 |

OTHER PUBLICATIONS

Codrich, Daniela. Applications and limits of raman spectroscopy in the study of colonic and pulmonary malformations. Diss. Università degli studi di Trieste, 2007. (Year: 2007).*

Amit Aggarwal, et al., "Multiphoton microscopy to identify and characterize the transition zone in a mouse model of Hirschsprung disease", J. Pediatric Surg. Jun. 2013, vol. 48, No. 6, pp. 1288-1293.

International Search Report and Written Opinion on PCT PCT/US2020/059539 Dtd Apr. 30, 2021 (17 pgs).

Invitation to Pay Additional Fees on PCT PCT/US2020/059539 Dtd Feb. 25, 2021 (3 pgs).

Marcos A. De Oliveira, et al., "Hyperspectral Raman microscopy can accurately differentiate single cells of different human thyroid nodules", Biomed Opt. Express, vol. 10, No. 9, Sep. 1, 2019, pp. 4411-4421.

* cited by examiner

LABEL-FREE SPECTRAL PATHOLOGY FOR IN VIVO DIAGNOSIS

CROSS-REFERENCE TO RELATED APPLICATIONS

The present application claims the benefit of and priority to U.S. Provisional Application No. 62/931,905, filed Nov. 7, 2019, the disclosure of which is incorporated herein by reference in its entirety.

TECHNICAL FIELD

The present invention relates generally to the field of histopathology, in particular, improved imaging modalities and methods for enhanced, label-free intraoperative histopathology.

BACKGROUND

Haemotoxylin and Eosin (H&E) histopathology, currently the "gold-standard" for pathological diagnosis of many diseases, can involve many tissue or biopsy sample preparation steps on time scales that are incompatible with intra-operative situations where quick decisions must be made. Advancing the field of pathology by developing new techniques capable of near real-time tissue analysis with the quality and accuracy that is comparable to or better than H&E would provide an invaluable tool for surgical guidance and improving clinical outcomes.

In particular, the patient management of Hirschsprung Disease could be significantly improved if a reliable diagnostic method was available that could more rapidly and accurately detect the presence or absence of intestinal ganglion cells. Such an approach could significantly reduce the overall time child patients are under anesthesia, improve clinical outcomes, and reduce the overall morbidity of HD. This disclosure satisfies this need and provides related advantages as well.

SUMMARY

The present disclosures overcomes the drawbacks of previously known methods by providing an improved method of intra-operative histopathology. In one embodiment of the methods, second harmonic generation (SHG) signals first identify the layers of a tissue that are suspected to be in close proximity to ganglion cells. These SHG signals are used to narrow down regions of interest that may contain ganglion cells. In some embodiments, the SHG signals come from collagen. An autofluorescence (AF) signal, such as a two-photon excitation AF signal, is also generated and provides a negative image contrast to further narrow down regions that may contain ganglion cells. In some embodiments, ganglion cells cannot emit an AF signal, and therefore the ganglion cells show up as dark, negative contrast regions in an AF image.

Both the SHG and AF signals provide an initial idea where ganglion cells can or may be in a region of interest, but their signatures are generally still not specific enough to surpass typical H&E stained biopsies. The present disclosure also identifies several Raman peaks that further distinguish ganglion cells and provide greater specificity and sensitivity in tissue biopsy.

Thus, a method for determining if a tissue is ganglionic is disclosed herein. The method can include and comprises, or consists essentially of, or yet further consists of: a) generating at least one hyperspectral Raman image of a tissue from a region of interest in a tissue suspected to contain ganglion cells that was optionally identified by a method comprising, or consisting essentially of, or yet further consisting of autofluorescence (AF) and Second Harmonic generation (SHG) imaging of the tissue; and b) analyzing any of the images for one or more of: i) optical excitation, ii) chemical information or emission spectra; or iii) AF, SHG, and/or Raman signatures, wherein the analysis provides indicators that the region of interest is either ganglionic or non-ganglionic. The method further can include identifying the tissue as ganglionic or non-ganglionic. For example, the image contrast provided by SHG and AF can enable visualization of overall tissue morphology and localization of regions that can or may have ganglion cells, while Raman signatures (RS) can provide detailed multiplexed molecular information that can be used to accurately identify specific ganglion cells.

In one aspect, the method further comprises, or consists essentially of, or consists of, or includes comparing an indicator from a region of interest to an indicator from a tissue adjacent to the region of interest. In some embodiments, the comparison includes analysis of a difference spectrum between tissue from a region of interest and an adjacent tissue, wherein an intensity peak on the difference spectrum at one of about 710 $cm^{-1}$, about 734 $cm^{-1}$, about 797 $cm^{-1}$, about 859 $cm^{-1}$, about 924 $cm^{-1}$, about 1216 $cm^{-1}$, about 1362 $cm^{-1}$, about 1440 $cm^{-1}$, or about 1660 $cm^{-1}$. The method can also be performed intraoperatively identifies a ganglionic tissue from a non-ganglionic tissue.

In some embodiments, the method can be performed in vivo. In certain embodiments, the method can be performed during a medical procedure or surgery.

The region of interest can also be identified by a method comprising, or consisting essentially of, or including autofluorescence. Autofluorescence imaging can also include negative contrast images. In some embodiments, autofluorescence can be two-photon autofluorescence. In certain embodiments, autofluorescence can be one-photon autofluorescence, optionally in a range of excitation wavelengths between about 375 nm to about 525 nm. Autofluorescence can also be tuned to different excitation wavelengths between about 750 nm to about 1050 nm. In some embodiments, the excitation wavelengths between about 750 nm to about 1050 nm for two-photon autofluorescence achieve the equivalent of about 375 nm to about 525 nm excitation using one-photon autofluorescence. Autofluorescence images can also be generated based on emission signals spanning from about 440 nm to about 700 nm.

In some embodiments, the region of interest can be identified by a method that comprises, or consists essentially of, or consists of, or includes Second Harmonic Generation (SHG). SHG can convert light of wavelength λ to light of wavelength λ/2. For purposes of the methods disclosed herein, wherein a laser can be tuned to a wavelength from about 700 nm to about 1600 nm and a bandpass filter centered at about 350 nm to about 800 nm can collect the SHG signal. In certain embodiments of the method, the laser can be tuned to a wavelength of about 930 nm and a bandpass filter centered at about 465 nm collects the SHG signal.

Hyperspectral Raman imaging can also constitute excitation wavelengths between about 785 nm to about 1085 nm using a tunable CW laser.

Analysis of spectra can include standard statistical analyses of Raman peak intensities. Analysis of spectra can also include multivariate statistical methods. For example, in some embodiments, multivariate statistical analyses can be performed by a method selected from at least one of principal component analysis (PCA), linear discriminant analysis (LDA), or leave-n-out cross validation methods. Any analysis of tissue data can be performed by a method selected from machine learning models, optionally including support vector machines (SVM) or non-probabilistic binary linear classifiers. For example, SVM, PCA, and LDA classification models can be applied to the hyperspectral Raman data to detect ganglion cells with a classification accuracy higher than 95 percent, enabling a near real-time, intraoperative histology method.

More than one hyperspectral Raman image can be mosaicked to generate a multidimensional Raman image of the tissue. In some embodiments, the Raman image can be mosaicked using at least one of a line scan microscope or a point scan microscope. In some embodiments, a plurality of pixel rows of the CCD chip of a detector collect all spectra in parallel and a motorized stage is used for lateral scanning and a piezo objective scanner is used for Z positioning.

In some embodiments of the methods, tissue samples from a region of interest can include murine tissue, porcine tissue, or human tissue. Tissue samples can be derived from whole tissue biopsy or cultured patient samples. The samples can be fresh, frozen, and preserved.

Brightfield images of tissues from a region of interest can also be generated, collected and analyzed for comparison with the AF, SHG, and Raman images.

In certain embodiments, the claimed methods are performed without any staining of the tissue samples. In certain further embodiments, tissue from the region of interest is further compared to tissue sample analyses performed using Haemotoxylin and Eosin (H&E) staining or calretinin immunohistochemistry to verify whether the region of interest tissues are normal or non-ganglionic.

The method can be performed in lieu of ex vivo H&E staining. Generating the at least one hyperspectral Raman image and analyzing the image (e.g., for one or more of optical excitation, chemical information or emission spectra, or AF, SHG, and/or Raman signatures) can also repeated more than once and using optical sectioning, z-stack imaging, and mosaicking to produce volumetric imaging of the region of interest without manual, physical sectioning.

In some embodiments of the methods, a continuous wave (CW) 785 nm laser is used for Raman excitation. Second Harmonic Generation signals can be excited using about 780 nm light and collected with a 390 nm bandpass filter in front of a PMT channel.

The claimed methods can be used to diagnose Hirschsprung disease.

A system for analysis of in vivo tissue or ex vivo tissue samples is also disclosed herein. The system can comprise of, or consist essentially of, or include a multiphoton autofluorescence microscope, a Second Harmonic Generation microscope, and a hyperspectral Raman microscope in operative communication. The Raman microscope can further comprise of, or consist essentially of, or consist of, or include a Raman excitation laser. In certain embodiments, the system further comprises, or consists essentially of, or consists of, or includes at least one of a Ti:Sapphire femtosecond laser or a CW laser. In certain embodiments, the system further comprises, or consists essentially of, or consists of, or includes motorized mirrors, optical shutters, a positioning stage, and software configured to provide hardware control and data acquisition from images generated by the microscopes.

The system can be housed in an endoscope configured to navigate intestinal tissue, colorectal tissue, or any tissue of the gastrointestinal tract. When unsectioned tissue is placed on a microscope the system can be automated to generate an AF/SHG image, pinpoint regions for further hyperspectral Raman analysis, acquire hyperspectral Raman data from said regions, optically section the tissue and repeat the measurement and analysis on another z-planes of the tissue, and compare spectra to a gold standard spectral database to arrive at a final tissue diagnosis. This automated process can be iterated more than once to create images that can be mosaicked to determine a larger field of view image.

In some embodiments, the system can be configured to acquire images at a tissue depth up to about 400 μm. The system can also be configured to be portable, sized to fit in an operating room, maneuverable on wheels, and activated and manipulated by a user intraoperatively. In certain embodiments, Raman spectroscopic signals can be detected using a spectrometer equipped with a spectral window of about 500 to about 2000 $cm^{-1}$ and a TE-cooled CCD camera.

BRIEF DESCRIPTION OF THE DRAWINGS

FIG. 9 (b1-b2) shows autofluorescence image of the ganglion cell region. The tissue emits AF, but the ganglion cell region does not. This negative contrast can potentially be used to locate the cells. FIG. 9 (c1-c2) show how SHG signals can assist in locating the tissue layers of interest. FIG. 9 (d1-d2) show more AF/SHG overlay images.

FIG. 10, bottom panel is a comparison of the Raman spectra from the negative AF region (i.e., ganglion cells) and adjacent non-ganglion or non-ganglionic cell tissue using PCA shows distinct groups, indicating that the spectra of the ganglion cells is distinct and unique.

DETAILED DESCRIPTION

Definitions

Figure 1:
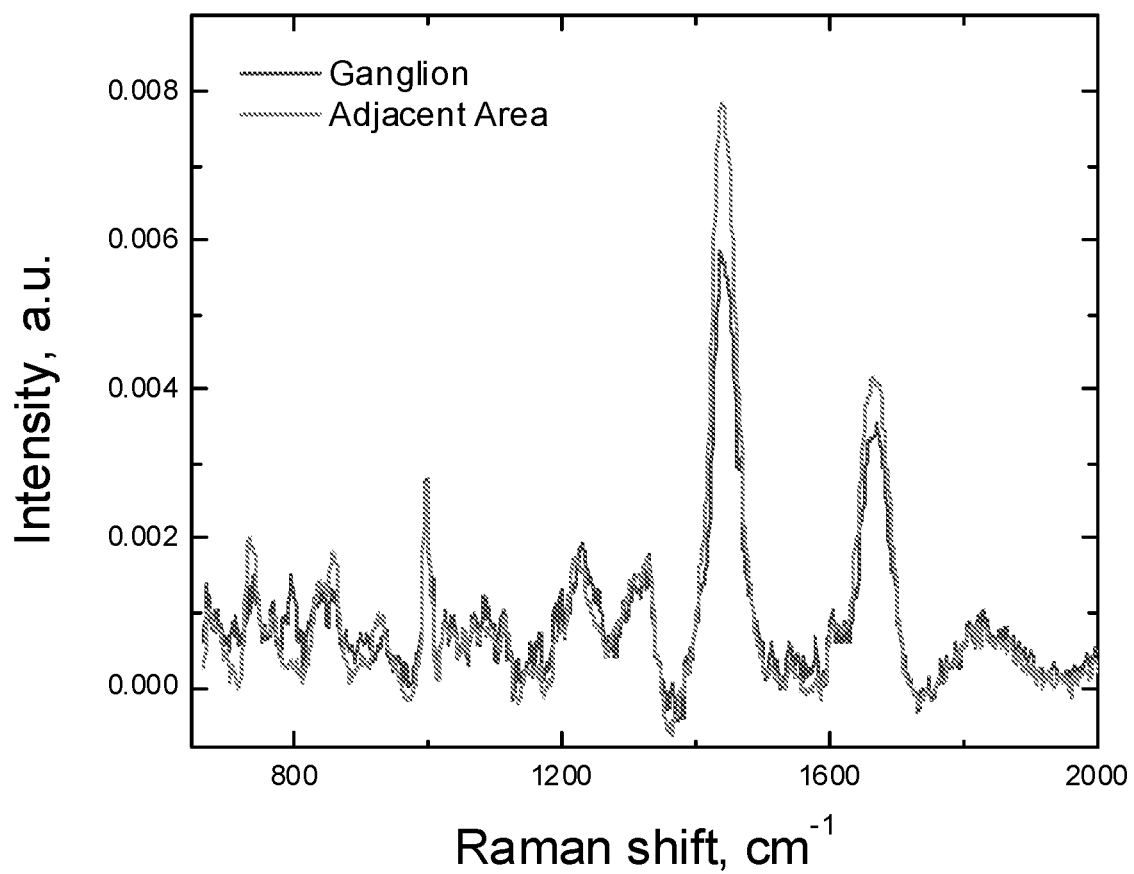
FIG. 1 is a graphical depiction of experimentally determined Raman peaks of ganglionic cells compared to those of adjacent non-ganglionic areas.

As used herein and in the appended claims, singular articles such as "a" and "an" and "the" and similar referents in the context of describing the elements are to be construed to cover both the singular and the plural, unless otherwise indicated herein or clearly contradicted by context.

As used herein, "about" is understood by persons of ordinary skill in the art and may vary to some extent depending upon the context in which it is used. If there are uses of the term which are not clear to persons of ordinary skill in the art given the context in which the term "about" is used, "about" will mean up to plus or minus 10% of the particular term.

As will be understood by one skilled in the art, for any and all purposes, all ranges disclosed herein also encompass any and all possible subranges and combinations of subranges thereof. Furthermore, as will be understood by one skilled in the art, a range includes each individual member.

The term "exemplary" as used herein refers to "serving as an example, instance, or illustration," and not "preferred" or "advantageous over other embodiments."

Unless defined otherwise, technical and scientific terms used herein have the same meaning as commonly understood by a person of ordinary skill in the art. In particular, this disclosure utilizes techniques in the field of optical spectroscopy and histopathology.

All numerical designations, e.g., pH, temperature, time, concentration, and molecular weight, including ranges, are approximations which are varied (+) or (−) by increments of 1.0 or 0.1, as appropriate or alternatively by a variation of +/− 15%, or alternatively 10% or alternatively 5% or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

As used herein, the term "comprising" is intended to mean that the devices, systems, compositions and methods include the recited elements, but do not exclude others. "Consisting essentially of" when used to define devices, systems, compositions and methods, shall mean excluding other elements of any essential significance to the combination for the intended use. "Consisting of" shall mean excluding more than trace elements of other elements and substantial method steps for administering the compositions disclosed herein. Embodiments defined by each of these transition terms are within the scope of this disclosure.

As used herein, "ganglionic" describes a structure or tissue containing a number of nerve cell bodies, typically linked by synapses, and often forming a swelling on a nerve fiber (i.e., containing ganglion). Conversely, a tissue that is "aganglionic" or "non-ganglionic" describes a structure or tissue that does not contain a number of nerve cell bodies, typically linked by synapses, and often forming a swelling on a nerve fiber (i.e., not containing ganglion). Parameters, indicators, and data points which determine the presence or absence of ganglionic tissue or cells are described throughout the specification.

As used herein, "region of interest" refers to areas of tissue or cells that are suspected to contain or have ganglion cells. In certain embodiments herein, regions of interest are initially determined based on results of autofluorescence, Second Harmonic Generation, and Brightfield imaging, and later verified using Raman signaling.

As used herein, "Second harmonic generation" (SHG, sometimes referred to as frequency doubling) can refer to a nonlinear optical process in which two photons with the same frequency interact with a nonlinear material, are "combined", and generate a new photon with twice the energy of the initial photons (equivalently, twice the frequency and half the wavelength).

Modes for Carrying Out the Disclosure

Systems and methods in accordance with the present disclosure overcome the drawbacks of previously known methods by providing an improved method of intra-operative histopathology. In one embodiment of the methods, second harmonic generation (SHG) signals first identify the layers of a tissue that are suspected to be in close proximity to ganglion cells. These SHG signals are used to narrow down regions of interest that may contain ganglion cells. In some embodiments, the SHG signals come from collagen. An autofluorescence (AF) signal is also generated and provides a negative image contrast to further narrow down regions that may contain ganglion cells. In one aspect of the disclosure, ganglion cells cannot emit an AF signal, and therefore the ganglion cells show up as dark, negative contrast regions in an AF image.

Both the SHG and AF signals provide an initial idea where ganglion cells may be in a region of interest, but their signatures are generally still not specific enough to surpass typical H&E stained biopsies. The present disclosure also identifies several Raman peaks that further distinguish ganglion cells and provide greater specificity and sensitivity in tissue biopsy.

Thus, a method for determining if a tissue is ganglionic is disclosed herein. The method can comprise of, or consist essentially of, or consist of, or include a) generating at least one hyperspectral Raman image of a tissue from a region of interest in a tissue suspected to contain ganglion cells that was optionally identified by a method comprising autofluorescence (AF) and Second Harmonic generation (SHG) imaging of the tissue; and b) analyzing any of the images for one or more of: i) optical excitation, ii) chemical information or emission spectra; or iii) AF, SHG, and/or Raman signatures, wherein the analysis provides indicators that the region of interest is either ganglionic or non-ganglionic. The method may further comprise, or consist essentially of, or consist of, or include identifying the tissue as ganglionic or non-ganglionic. At least one of the AF or SHG signals can be evaluated to detect a contrast between at least a first region and a second region (which can be adjacent to the first region), and a candidate region potentially having ganglionic cells detected from the first region responsive to the contrast satisfying a threshold (e.g., the contrast is a sufficiently negative contrast to satisfy the threshold; the threshold can be determined based on validating the threshold using tissue stained image data).

In some embodiments, the method further comprises, or consists essentially of, or consists of, or includes comparing an indicator from a region of interest to an indicator from a tissue adjacent to the region of interest. In one aspect of the method, the comparison comprises, or consists essentially of, or consists of, or includes analysis of a difference spectrum between tissue from a region of interest and an adjacent tissue, wherein an intensity peak on the difference spectrum at one of about 710 $cm^{-1}$, about 734 $cm^{-1}$, about 797 $cm^{-1}$, about 859 $cm^{-1}$, about 924 $cm^{-1}$, about 1216 $cm^{-1}$, about 1362 $cm^{-1}$, about 1440 $cm^{-1}$, or about 1660 $cm^{-1}$ identifies a ganglionic tissue from a non-ganglionic tissue. The method can be performed in vivo or in vitro, or ex vivo. In certain embodiments, the method is performed intraoperatively, such as during a medical procedure or surgery. In some aspects of the disclosure, the region of interest is identified by a method that comprises, or consists essentially of, or consists of, or includes autofluorescence. Autofluorescence imaging can also comprise, or consist essentially of, or consist of, or include negative contrast images. In some embodiments, autofluorescence can be two-photon autofluorescence. In a certain embodiment, autofluorescence may or can be one-photon autofluorescence, optionally in a range of excitation wavelengths between about 375 nm to about 525 nm. Autofluorescence can also be tuned to different excitation wavelengths between about 750 nm to about 1050 nm. In another aspect of the disclosure, the excitation wavelengths between about 750 nm to about 1050 nm for two-photon autofluorescence achieve the equivalent of about 375 nm to about 525 nm excitation using one-photon autofluorescence. Autofluorescence images can also be generated based on emission signals spanning from about 440 nm to about 700 nm.

In an aspect of the disclosure, the region of interest may also be identified by a method comprising SHG Second harmonic generation can convert light of wavelength λ, to light of wavelength λ/2. For purposes of the methods disclosed herein, wherein a laser can be tuned to a wavelength from about 700 nm to about 1600 nm and a bandpass filter centered at about 465 nm collects the SHG signal. In certain embodiments of the method, the laser can be tuned comprising λ wavelength of about 930 nm and λ/2 of about 465 nm and a bandpass filter centered at λ/2 to collect the SHG signal.

Hyperspectral Raman imaging can constitute excitation wavelengths between about 785 nm to about 1085 nm using a tunable CW laser.

Analysis of spectra can include standard statistical analyses of Raman peak intensities. Analysis of spectra can also include multivariate statistical methods. For example, in some embodiments, multivariate statistical analyses can be performed by a method selected from at least one of principal component analysis, linear discriminant analysis, or leave-n-out cross validation methods. Any analysis of tissue data can be performed by a method selected from machine learning models, optionally including support vector machines (SVM) or non-probabilistic binary linear classifiers.

More than one hyperspectral Raman image can be mosaicked to generate a multidimensional Raman image of the tissue. In some embodiments, the Raman image can be mosaicked using at least one of a line scan microscope or a point scan microscope. A plurality of pixel rows of the CCD chip of a detector collect all spectra in parallel and a motorized stage is used for lateral scanning and a piezo objective scanner is used for Z positioning.

In a further aspect of the disclosure, tissue samples from a region of interest can comprise murine tissue, porcine tissue, or human tissue. Tissue samples can be derived from whole tissue biopsy and/or patient samples that can be fresh or preserved.

Brightfield images of the tissues can also be collected and analyzed for comparison with the AF, SHG, and Raman images.

In certain embodiments, the claimed methods are performed without any staining of the tissue samples. In certain further embodiments, tissue from the region of interest is further compared to tissue sample analyses performed using Haemotoxylin and Eosin (H&E) staining or calretinin immunohistochemistry to verify whether the region of interest tissues are normal or non-ganglionic.

The method can or may be performed in lieu of ex vivo H&E staining. Generating the at least one hyperspectral Raman image and analyzing the image (e.g., for one or more of optical excitation, chemical information or emission spectra, or AF, SHG, and/or Raman signatures) can also repeated more than once and using optical sectioning, z-stack imaging, and mosaicking to produce volumetric imaging of the region of interest without manual, physical sectioning.

In some embodiments of the methods, a continuous wave (CW) 785 nm laser is used for Raman excitation. Second Harmonic Generation signals can be excited using about 780 nm light and collected with a 390 nm bandpass filter in front of a PMT channel.

The claimed methods can be used to diagnose conditions including but not limited to Hirschsprung disease. For example, responsive to determining that the tissue is ganglionic, one or more conditions can be diagnosed. For example, an amount (e.g., count, density, size, or other parameter determined from the Raman spectroscopy data) can be compared to at least one of a minimum threshold or a maximum threshold indicative of the condition to diagnose the condition responsive to the amount satisfying the at least one of the minimum threshold or the maximum threshold (e.g., determining Hirschsprung disease to be present responsive to a count of ganglionic cells in a volume of tissue being greater than a threshold count).

A system for analysis of in vivo tissue or ex vivo tissue samples is also disclosed herein. The system can comprise, or consist essentially of, or consist of, or include a multiphoton autofluorescence microscope, a Second Harmonic Generation microscope, and a hyperspectral Raman microscope in operative communication. The Raman microscope can further comprise, or consist essentially of, or consist of, or include a Raman excitation laser. In certain embodiments, the system further comprises, or consists essentially of, or consists of, or includes at least one of a Ti:Sapphire femtosecond laser or a CW laser. In certain embodiments, the system further comprises, or consists essentially of, or consists of, or includes motorized mirrors, optical shutters, a positioning stage, and software configured to provide hardware control and data acquisition from images generated by the microscopes.

The system can be housed in an endoscope configured to navigate intestinal tissue, colorectal tissue, or any tissue of the gastrointestinal tract. When unsectioned tissue is placed on a microscope the system can be automated to generate an AF/SHG image, pinpoint regions for further hyperspectral Raman analysis, acquire hyperspectral Raman data from said regions, optically section the tissue and repeat the measurement and analysis on another z-planes of the tissue, and compare spectra to a gold standard spectral database to arrive at a final tissue diagnosis. This automated process can be iterated more than once to create images that can be mosaicked to determine a larger field of view image.

Figure 3:
FIG. 3 depicts the challenge that surgeons face in determining how much colon to resect. Excessive removal of healthy bowel or incomplete resection are both undesirable. H&E staining of multiple biopsies is often required.

In some embodiments, the system can be configured to acquire images at a tissue depth up to about 400 µm. The system can also be configured to be portable, sized to fit in an operating room, maneuverable on wheels, and activated and manipulated by a user intraoperatively. In certain embodiments, Raman spectroscopic signals can be detected using a spectrometer equipped with a spectral window of about 500 to about 2000 $cm^{-1}$ and a TE-cooled CCD camera.
Comparisons with Current Protocol for Histopathological Analysis In surgical treatment of conditions such as Hirschsprung Disease, surgeons typically perform a pull-through procedure in which a non-ganglionic segment of the intestine is removed and the remaining healthy intestine is attached to the anus. To guide the surgeon in identifying the boundary between the healthy and diseased regions of the intestine, several biopsies that undergo histopathological analysis are required. A biopsy is initially performed close to the anus, which is delivered to the pathology lab and processed (i.e., sectioned & H&E stained). The slides are reviewed by a pathologist to determine if ganglion cells are present. If ganglion cells are not detected, another biopsy needs to be performed higher up in the intestine. This process may need to be repeated several times until a biopsy sample comes back positive for ganglion cells. This long process can add a considerable amount of time to the surgical procedure. This process requires intraoperative surgical biopsies at multiple levels of the distal bowel (FIG. 3) to identify the extent of abnormal intestine, often adding hours to an operation while a child is under general anesthesia. FIG. 3 shows the challenge that surgeons face in determining how much colon to resect. Excessive removal of healthy bowel or incomplete resection are both undesirable. H&E staining of multiple biopsies is often required. Procedures can be performed as described herein in which the removed tissue can be analyzed using imaging techniques to detect ganglionic or non-ganglionic cells, enabling intra-operative detection times.

Figures 4A, 4B, 4C:
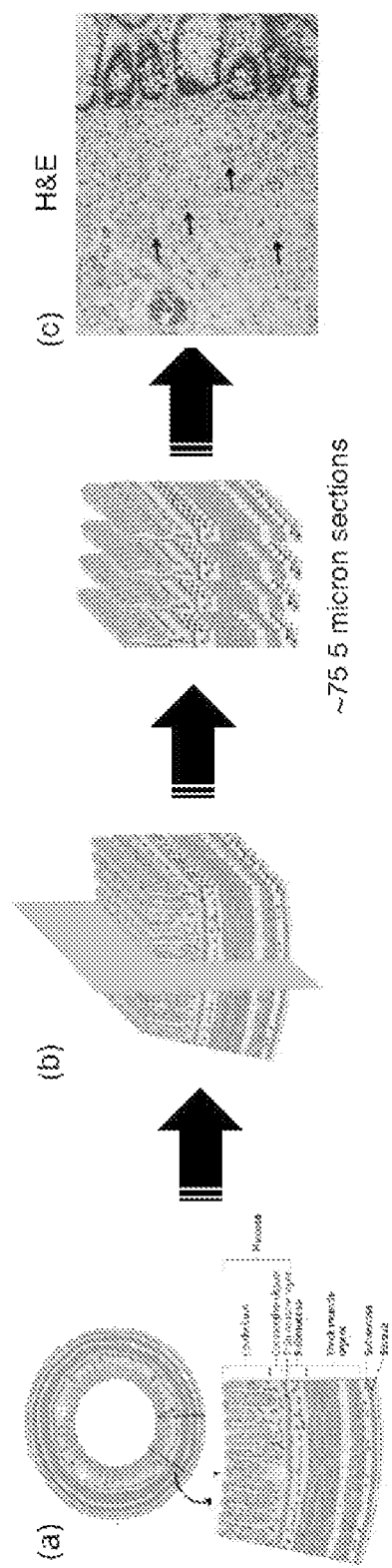
FIG. 4(a) shows that biopsies of intestinal tissue can contain multiple layers, from the mucosa to the serosa. As depicted in FIG. 4(b) the biopsy is physically sectioned, typically up to seventy-five 5 μm sections to ensure thorough examination for the presence/absence of ganglion cells.
FIG. 4(c) shows H&E staining is often used to image each tissue section and to identify ganglion cells (arrows).

FIG. 4 (a) is an illustration of the cross section of intestinal tissue showing different layers. The ganglion cells form the network of nerves called the myenteric plexus (Auerbach plexus) located between the smooth muscle layers of the GI tract wall and the submucosal plexus (Meissner plexus) within the submucosa of the GI tract wall. A tissue biopsy, millimeters in dimension, usually includes all layers. In a typical protocol, the tissue biopsy is sectioned into 15 serial 5 µm thick slices. This initial 'pilot' section is H&E stained and examined for the presence of ganglion cells. If none are present, another about 60 serial sections are prepared and examined. These about 75 serial sections, amounting to a total of about 375 µms of tissue, are typically sufficient to perform an assessment of whether the biopsy sample is normal or non-ganglionic. As depicted in FIG. 4(b) the biopsy can be physically sectioned, typically up to seventy-five 5 µm sections to ensure thorough examination for the presence/absence of ganglion cells. FIG. 4(c) shows H&E staining is often used to image each tissue section and to identify ganglion cells (arrows).

In certain embodiments of the proposed methods, a fresh biopsy sample is obtained by the surgeon and analyzed at the surgeon's side to provide immediate, accurate, objective diagnosis of the tissue. As such, the sometimes repetitive and time consuming processes involved with delivering, processing (sectioning, staining), and analyzing the specimen at the pathology lab can be circumvented. Table 1 summarizes the key advantages of the proposed technology compared to current H&E histopathology.

TABLE 1

Efficiency and Diagnostic Advantages of Multimodal, Label-Free Imaging

|  | Current H&E | Proposed Technology |
| --- | --- | --- |
| Sample Handling | Transportation of biopsy sample from surgery to pathology lab | Measurement made at surgeon's side |
| Sample Processing | Physical sectioning of about 75 five micron thick sections H&E staining | Fresh, whole tissue analysis Optical sectioning capability Label-free, no stains |
| Sample Analysis | Pathologist interpretation Results communicated back to surgeon | Chemical information for accurate, objective diagnosis Information directly to surgeon |

Figure 5:
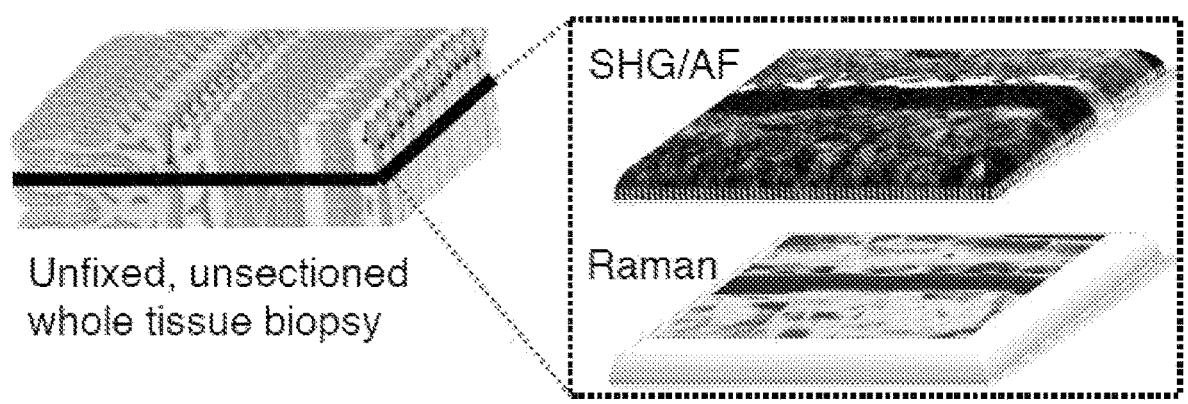
FIG. 5 illustrates multimodal, label-free spectral histopathology with AF/SHG/Raman modalities, enabling high resolution optical sectioning and imaging on a fresh tissue biopsy that is several hundred microns thick. The chemical information provided by these modalities enable localization and identification of ganglion cells.
Figure 6:
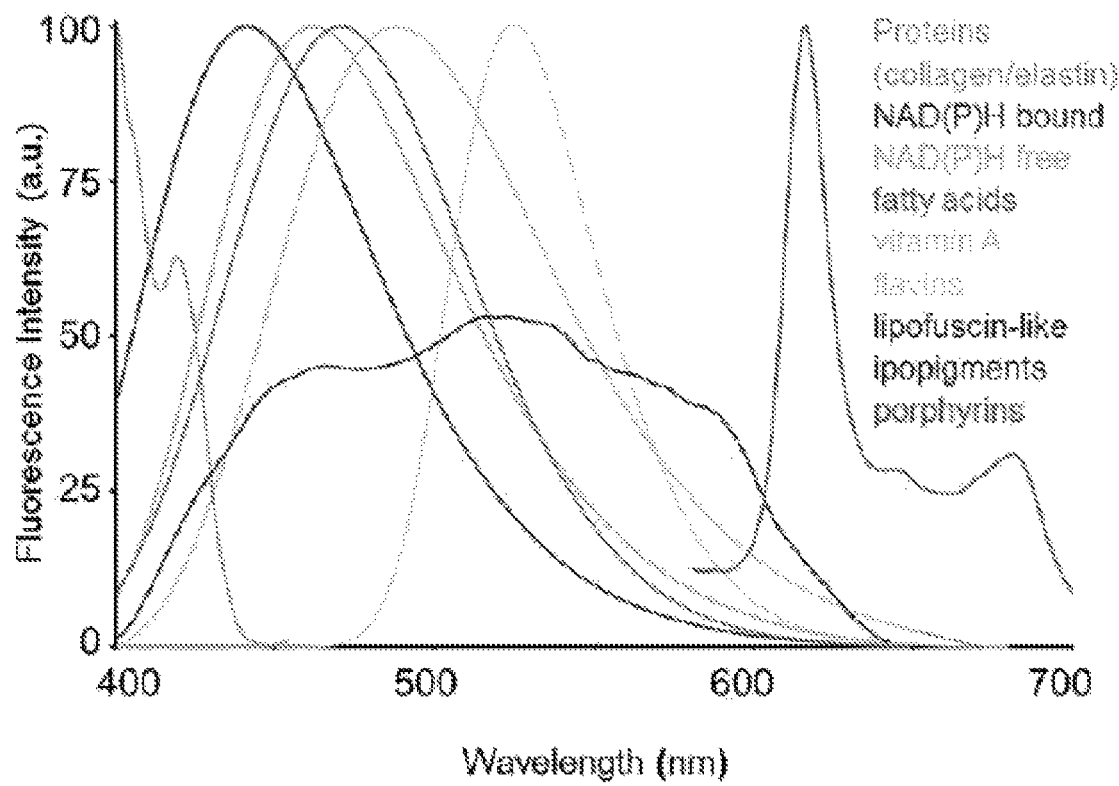
FIG. 6 is a graphical depiction of native autofluorescence from different endogenous fluorophores in biological tissues.

FIG. 5 illustrates multimodal, label-free spectral histopathology with AF/SHG/Raman modalities, enabling high resolution optical sectioning and imaging on a fresh tissue biopsy that is several hundred microns thick. The chemical information provided by these modalities enable localization and identification of ganglion cells. The confocal and multiphoton nature of these optical methods enable high-resolution deep tissue imaging that can cover the about 400 µms of tissue typically used by pathologists to assess a biopsy sample. (In fact, up to 800 µms of tissue can be analyzed by interrogating both sides of the biopsy sample). This analysis can be performed directly on fresh tissue without needing to fix and section. The label-free capabilities of these techniques can provide morphological and chemical information without needing stains or labels. The optical signals that are acquired directly from the tissue are unique chemical fingerprints that can be used for highly specific, accurate, and objective identification of ganglion cells to minimize the subjectivity of human analysis and interpretation.
Two Photon Excited Autofluorescence Autofluorescence (AF) signals emitted from endogenous fluorophores can be used as an image contrast for obtaining morphological, structural and chemical information of biological tissues. These fluorophores are used for a broad range of applications, such as monitoring metabolic functions of cells and tissues under normal and experimental conditions or for real-time diagnosis of oncological and other diseases. For example, NAD(P)H and flavins are two of the most extensively studied endogenous fluorophores. NAD(P)H is fluorescent in the reduced state and flavins in the oxidized state, and the AF emission properties are strongly dependent on the bound/free condition of these molecules. Hence, the ratiometric measurement of these two molecules can provide information about energetic metabolism, cell oxidative defense, biosynthesis, and signal transduction. Lipofuscin and lipofuscin-like lipopigments are another type of fluorophore whose fluorescence properties depend on composition, crosslinks and oxidation degree, and aging. Lipofuscins can be present in undigested material remaining from phagocytosis and autophagy processes, accumulating as intracytoplasmic granules depending on physiological and metabolic situations. This signal has been used to monitor oxidative stress as a response to pathological conditions (e.g., Batten disease) or to measure the toxic effects of compounds. There are many other endogenous fluorophores that are excited and emit fluorescence at different wavelengths. FIG. 6 shows the spectral profile of many molecules that can contribute to AF in biological materials. These signals can be generated using either one-photon or two-photon excitation. Regions that have ganglion cells can have lower AF signals compared to adjacent tissue, resulting in these regions having a negative contrast in the AF images.

Second Harmonic Generation

Second harmonic generation (SHG) is a label-free non-linear optical technique that can directly detect the presence of specific biomolecules that have a unique, intrinsic molecular symmetry structure. This technique is based on the unique optical property of certain molecules to convert light of wavelength $\lambda$, to light of wavelength $\lambda/2$ because of their non-centrosymmetric ordered molecular structure. Primarily implemented as an optical imaging technique, SHG microscopy has previously been used to image the myosin rod bundles in cardiomyocytes and collagen in tissue. The SHG signal can be strongly detected from connective tissue rich in collagen (e.g., from a submucosal region), thus providing an optical marker for detection of the orientation of an unstained tissue section.

Figures 7A, 7B, 7C:
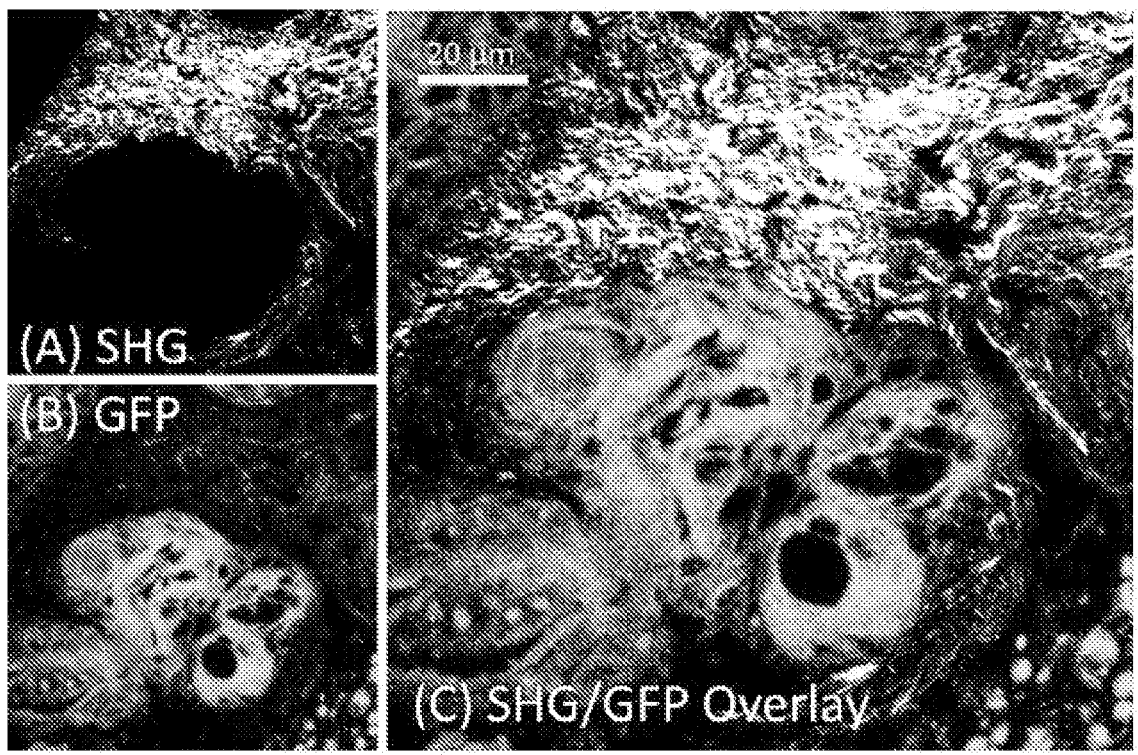
FIG. 7(a) shows an example of a tissue image taken with Second Harmonic Generation (SHG) alone.
FIG. 7(b) depicts fluorescence signals from green fluorescent protein labeled oral squamous cell carcinoma acquired simultaneously with a multiphoton microscope. Green fluorescent protein labels the cell membrane and SHG signals originate from collagen around the cells.
FIG. 7(c) shows an overlay image of both SHG and GFP fluorescence images.

FIG. 7 shows an example of multimodal label-free imaging of tumor (oral cancer) tissue that uses a combination of two photon fluorescence microscopy to image the GFP labeled tumor cells and SHG microscopy to image the surrounding collagen due to fibrosis. A Ti:Sapphire femtosecond laser tunable from about 750-1000 nm is the excitation source. The laser beam can be focused onto the sample with a high numerical aperture objective (NA=1.2) and can be scanned across the sample using an inverted laser scanning confocal microscope. The laser can be tuned to a wavelength $1=930$ nm and a PMT with a bandpass filter centered at $\lambda/2=465$ nm collects the SHG signal. Another PMT with a 510-590 nm filter collects the GFP signal from the tumor cells (green). Note that although SHG signals are known to propagate primarily in the forward direction due to phase matching conditions and is measured using a detector in the forward position, SHG signals can also be detected in the backward direction as well (not shown). This ratio of forward to backward signals can provide additional information about the degree of collagen fiber ordering. FIG. 7(a) shows an example of a tissue image taken with Second Harmonic Generation (SHG) alone. FIG. 7(b) depicts fluorescence signals from green fluorescent protein labeled oral squamous cell carcinoma acquired simultaneously with a multiphoton microscope. Green fluorescent protein labels the cell membrane and SHG signals originate from collagen around the cells. FIG. 7(c) shows an overlay image of both SHG and GFP fluorescence images.

Hyperspectral Raman Microscopy

Figure 8:
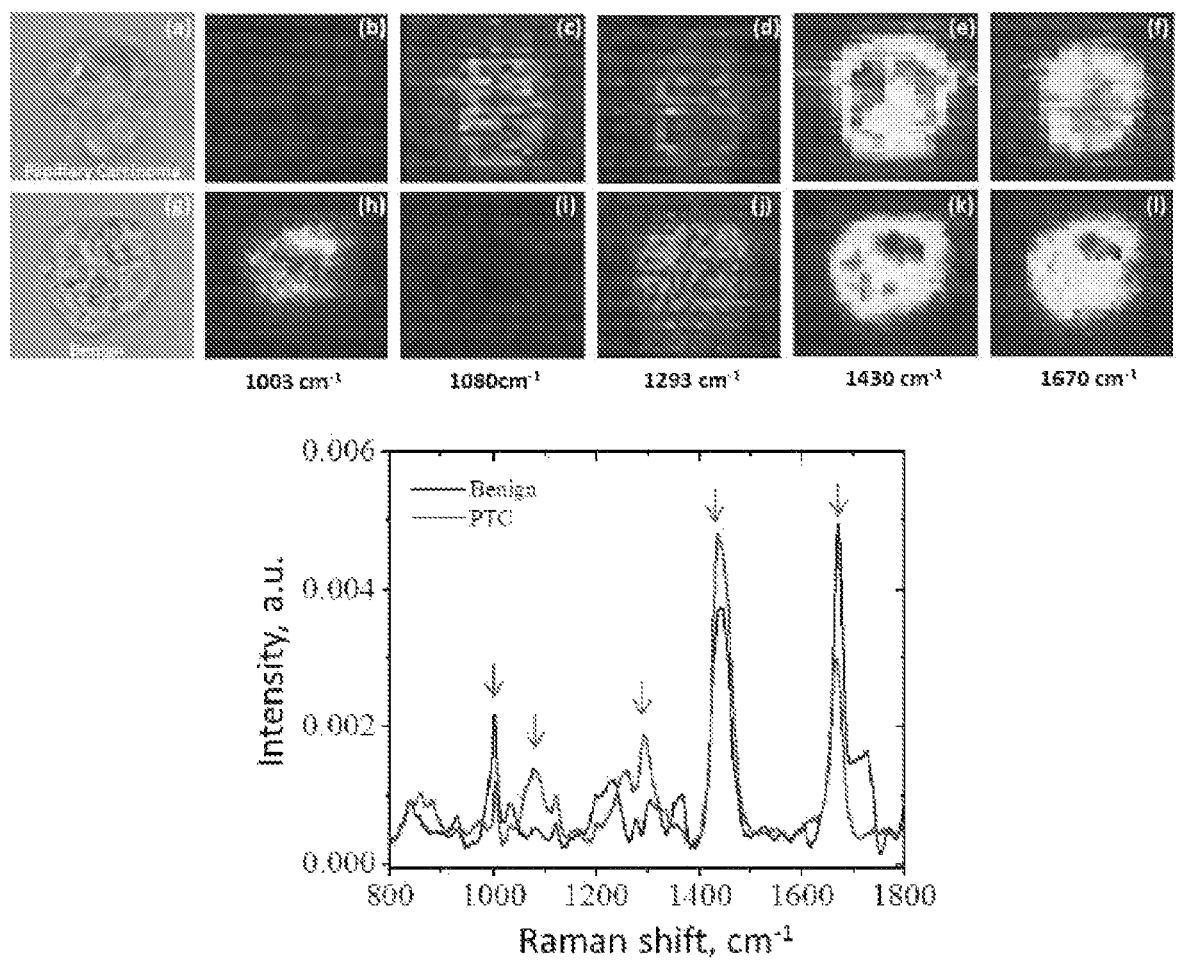
FIG. 8, top panel, shows Brightfield and Raman images of papillary thyroid carcinoma (PTC) and benign thyroid cells. Each Raman image is based on the signal intensity of specific Raman peaks associated with different biomolecules (DNA, phenylalanine, protein). The bottom panel of FIG. 8 is a graphical representation of whole cell averaged Raman spectra of benign and PTC cells showing spectral differences (arrows) that can be used to discriminate these two cell types.

FIG. 8 top panel applies hyperspectral Raman microscopy to image benign and malignant thyroid cells and the use of Raman spectra as a label-free molecular fingerprint for objective identification and classification of these cells. Because Raman signals are intrinsic to the sample, Raman microscopy enables label-free, non-invasive imaging of the intrinsic biochemistry of the specimen. The hyperspectral nature of Raman spectroscopy provides a wealth of molecular information of the specimen in a single interrogation without requiring the use of multiple labels. Raman spectroscopy also offers the potential for discovering new label-free spectral signatures for characterizing and identifying cell types.

Figures 9A, 9B, 9C, 9D:
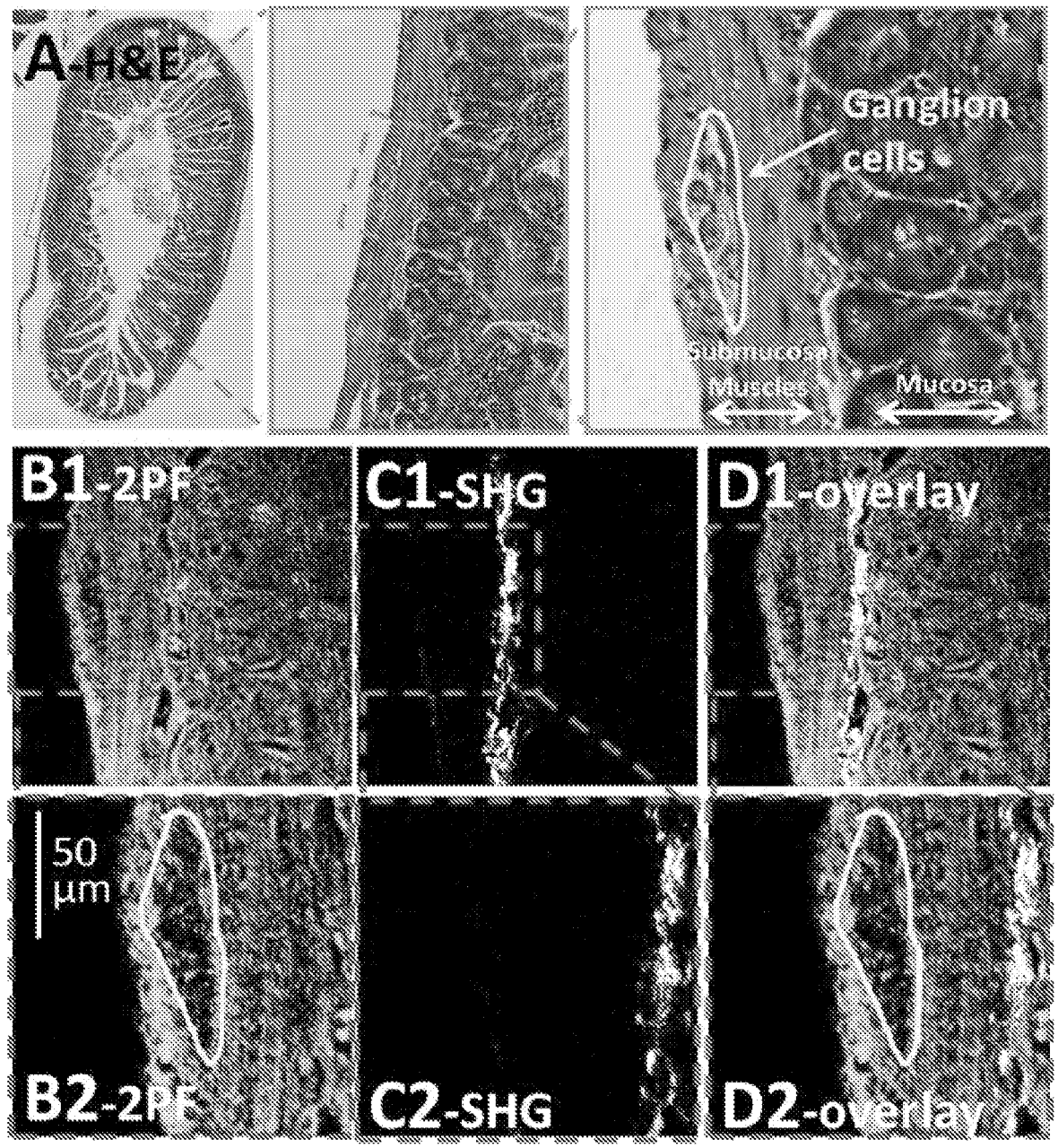
FIG. 9 (a) shows H&E imaging showing the location of ganglion cells in the submucosal region.

FIG. 9 shows results of two adjacent 5 µm thick tissue sections imaged by H&E and AF/SHG. H&E imaging has been seen as the gold standard in the art for definitively locating and identifying ganglion cells, but a comparison of the AF/SHG image to the H&E image shows useful information provided in the AF/SHG image for narrowing down the locations of the ganglion cells. First, the SHG signals, which come from collagen, provide a visual marker for locating the submucosa and muscle layers and, in combination with the outer edge of the tissue (serosa), can be used to narrow down the location of the ganglion cells in the tissue. The AF signal is also an important image contrast agent to visualize the morphology and structure of the tissue specimen. Specifically, most of the tissue emits AF signals, but the ganglion cells do not. As such, the ganglion cells can potentially be located based on the negative image contrast in the AF image.

The negative contrast in FIG. 9 suggests a region that may contain ganglion cells. Although this negative contrast in combination with the SHG signals can help pinpoint regions that possibly contain ganglion cells, there are other regions with a negative AF contrast that do not correlate with ganglion cells in the H&E image. To determine if Raman spectroscopy can provide a more definitive optical signature for identifying ganglion cells, Raman spectra are acquired from different regions of the tissue. Comparison of the Raman spectra from the ganglion cells to spectra of other locations of the tissue can be performed using both standard statistical analysis of the Raman peak intensities and more sophisticated multivariate statistical methods (principal component analysis, linear discriminant analysis, leave-n-out cross validation) to determine unique Raman spectral features of ganglion cells.

Figure 10:
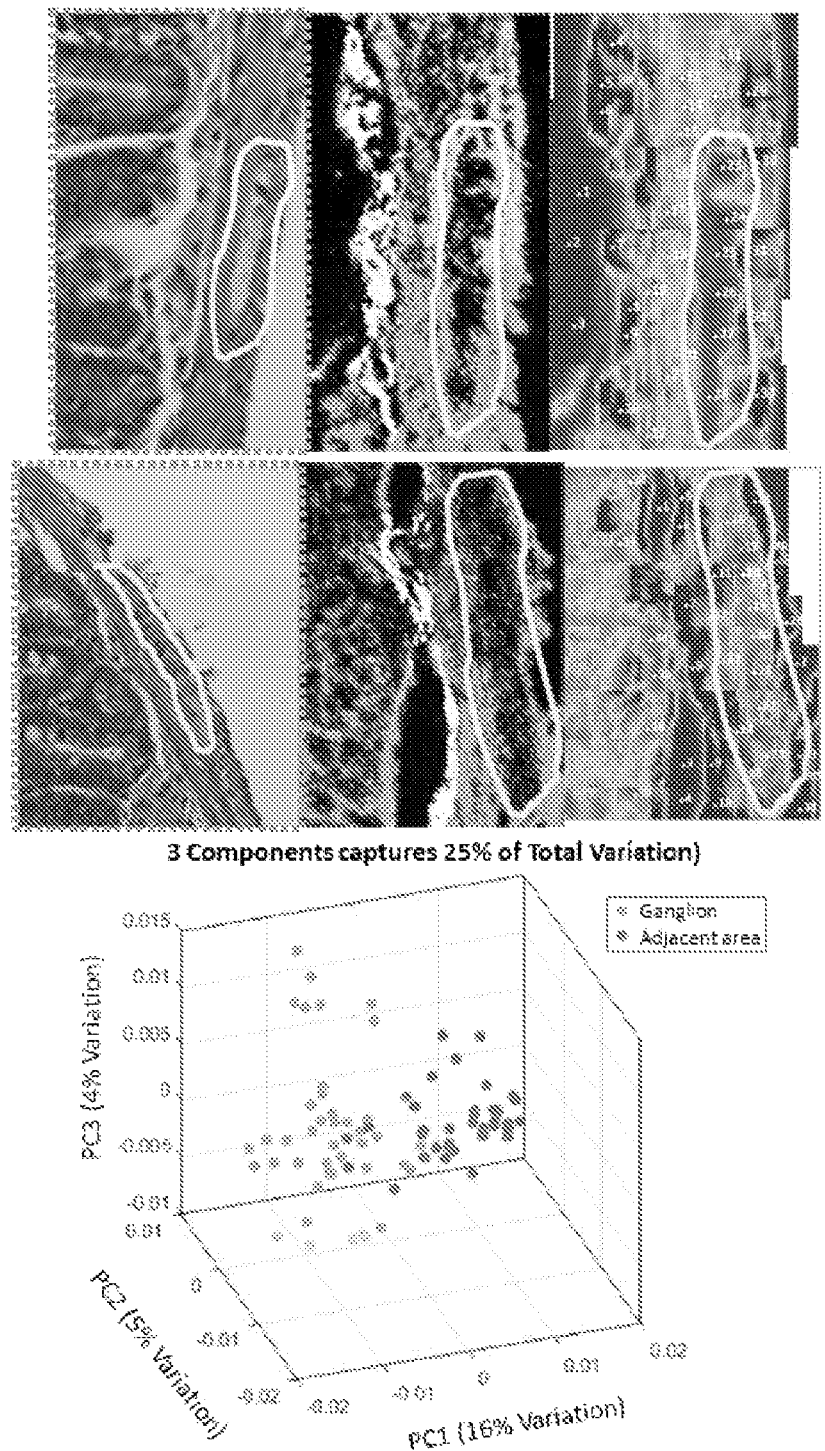
FIG. 10, top panel shows H&E, AF/SHG, and hyperspectral Raman images of normal tissue from wild type mice. The AF/SHG and Raman images were acquired from the same sample. Yellow circles denote the ganglion cell region.

FIG. 10 shows data of Raman images acquired from tissues that were also imaged with AF/SHG and H&E (adjacent tissue). H&E images confirm the location of the ganglion cells and the AF/SHG images highlight those same regions that contain ganglion cells by the negative AF contrast. The Raman images are composed of 8-10 Raman images that are stitched together to form the final image of the tissue. Note that the entire Raman image took about 2 hours to acquire. This time-intensive Raman imaging is essential in this task for comprehensive analysis of the entire tissue. With these hyperspectral Raman images, Raman spectrum can be extracted from all parts of the tissue and compare the spectra of the ganglion cell regions to the spectra of other tissue regions.

The following examples are provided to illustrate and not limit this disclosure.

EXAMPLES

Example 1: Determining the Unique Optical Signatures for Identifying Ganglion Cells Using Intestinal Tissue Sections from Wild Type Mice and a Knockout Mouse Model of HD Preparation of Adjacent Tissue Sections for H&E Staining and Label-Free Imaging Colon from three-week-old C57/BL6 wild type mice and three-week-old homozygous endothelin receptor B(EdnrB)

knockout mice, a known murine model of HD is obtained and formalin fixed. Following paraffin embedding, adjacent 5 µm sections are prepared. These adjacent sections are deparaffinized and alternately stained with H&E or remain unstained for label-free HG/AF/Raman imaging. Submucosal and myenteric ganglion cells are identified as those with large, round well-defined nuclei and abundant cytoplasm as per standard H&E. Because ganglion cells are large enough to span multiple adjacent 5 µm sections, this method allows for comparison of standard H&E histopathology and label-free imaging in near identical samples. A clinical gastrointestinal pathologist confirms the location of ganglion cells on H&E histopathology.

AF/SHG Microscopy to Locate Ganglion Cells in Tissues from Wild Type Mice

Simultaneous AF and SHG microscopy is performed on the unstained tissue sections using a home-built multiphoton AF/SHG microscope. Briefly, an Olympus Fluoview 300 inverted scanning confocal microscope is equipped with multiple ports that allow for simultaneous detection of both AF and SHG signals. A Ti:Sapphire femtosecond laser is used for exciting both SHG and two photon autofluorescence. In one channel, SHG signals are detected using a bandpass filter with a center wavelength at half the excitation wavelength. In the second channel, AF signals generated via two photon excitation are detected using a bandpass filter matching the emission spectrum. For example, an excitation wavelength of 940 nm would yield an SHG signal at 470 nm, and a fluorescence signal from 510-590 nm. FIG. 9 shows preliminary results of two adjacent 5 µm thick tissue sections imaged by H&E and AF/SHG. The H&E image is used as the gold standard for definitively locating and identifying ganglion cells. A comparison of the AF/SHG image to the H&E image shows potentially useful information provided in the AF/SHG image for narrowing down the locations of the ganglion cells. First, the SHG signals, which come from collagen, provide a visual marker for locating the submucosa and muscle layers and, in combination with the outer edge of the tissue (serosa), can be used to narrow down the location of the ganglion cells in the tissue. The AF signal is also an important image contrast agent to visualize the morphology and structure of the tissue specimen. Specifically, most of the tissue emits AF signals, but the ganglion cells do not. As such, the ganglion cells can potentially be located based on the negative image contrast in the AF image.

More samples of normal, healthy tissues can be analyzed from wild type mice that contain ganglion cells to provide more robust data. It is necessary to establish whether there is a positive correlation between the negative contrast observed in the AF/SHG images and the ganglion cells in the H&E images. SHG signals are used to help pinpoint regions of interest. The effect of different excitation wavelengths on the AF images is also investigated. Tuning the excitation from about 750-1050 nm to achieve the equivalent of 375-525 nm one-photon excitation, AF images are generated based on emission signals spanning from 440 to 700 nm that reflect the range of different intrinsic biomolecules listed in FIG. 6. The different AF images are compared to the H&E images to determine the optimal excitation/emission wavelengths for locating ganglion cells. In some embodiments, optimal excitation/emission wavelength can: 1) reduce the number of negative contrast non-ganglion cell regions to improve the localization of ganglion cell regions or 2) generate a brighter AF of the ganglion cells above the tissue AF to positively identify the cells.

Hyperspectral Raman Microscopy for Chemical Signatures of Ganglion Cells

Figure 2:
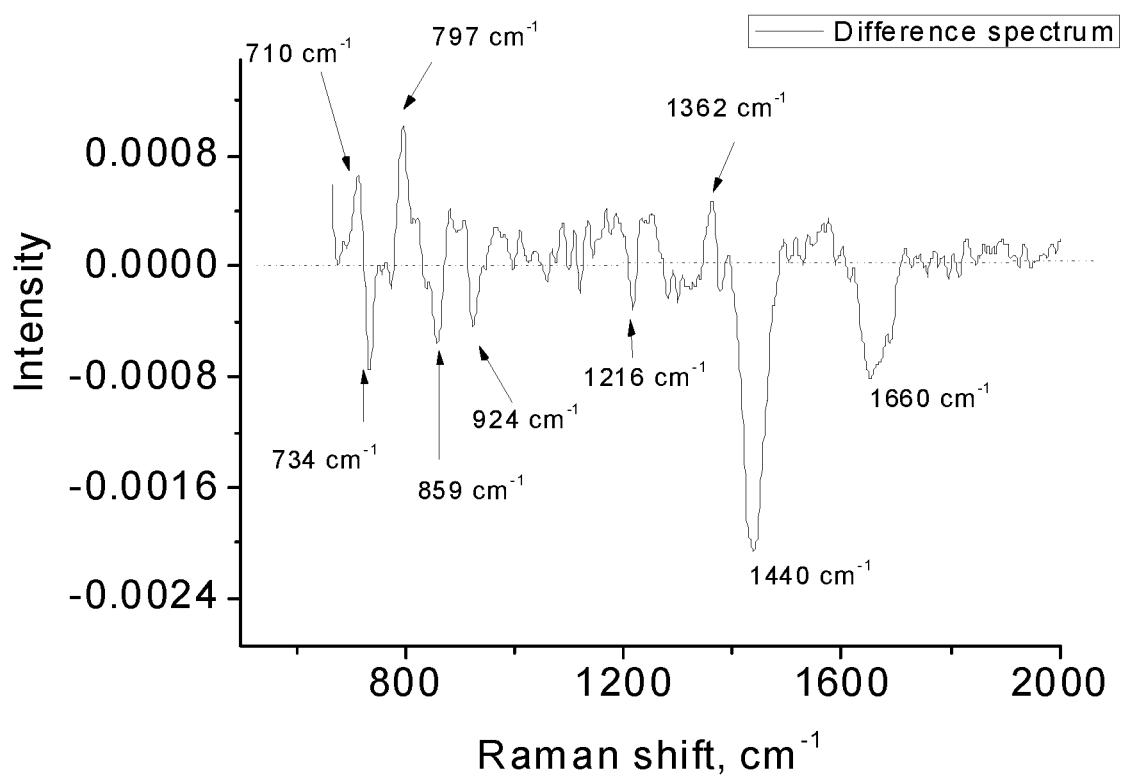
FIG. 2 is a graphical depiction of the separation in intensity (a.u.) for Raman shift wavelengths between ganglionic and adjacent tissue area shown as a difference spectrum.

The negative contrast in FIG. 9 suggests a region that may contain ganglion cells, as regions potentially having ganglion cells (e.g., candidate regions) can have lower AF signals compared to adjacent tissues, demonstrating that SHG/AF can be used to rapidly survey the tissue to detect the candidate regions. Although this negative contrast in combination with the SHG signals can help pinpoint regions that possibly contain ganglion cells, there are other regions with a negative AF contrast that do not correlate with ganglion cells in the H&E image. To determine if Raman spectroscopy provide a more definitive optical signature for identifying ganglion cells, Raman spectra are acquired from different regions of the tissue. Comparison of the Raman spectra from the ganglion cells to spectra of other locations of the tissue is performed using both standard statistical analysis of the Raman peak intensities and more sophisticated multivariate statistical methods (principal component analysis, linear discriminant analysis, leave-n-out cross validation). Unique Raman spectral features of ganglion cells are determined, for example, as shown in FIG. 1 and FIG. 2. In FIG. 1, the intensity of the scattered light (y-axis) is plotted against each energy (frequency) of light (x-axis). The frequency is measured in a unit called the wavenumber (number of waves per cm, i.e., $cm^{-1}$) and the scattered light is measured in a.u. or arbitrary units. FIG. 2 depicts the separation in intensity between ganglionic and adjacent area Raman spectra as a difference spectrum. The difference spectrum shows peaks that potentially identify ganglion cells from non-ganglion adjacent regions.

Hyperspectral Raman images can then be acquired from the same tissue regions that were imaged by AF/SHG. A home-built line scan Raman microscope is used to acquire multiple Raman images, which are mosaicked to generate the Raman image of the tissue. This line scan microscope can generate Raman images faster than traditional single focus Raman microscopes because of its parallel spectral detection capability. The Raman microscope is equipped with a 2 W continuous wave (CW) laser with a wavelength of 785 nm that is used as the excitation source. The laser beam is shaped into a line using a cylindrical lens and confocality is ensured by a slit at the entrance of the spectrometer. A 60×/1.2 NA oil immersion objective is used to focus the line shaped beam onto the sample and to collect Raman spectra from each position along the laser line. The Raman spectra are projected through the spectrometer slit and onto a 1340×100 pixel CCD camera. The 100 pixel rows collect all spectra in parallel. A motorized stage is used for lateral scanning and a piezo objective scanner is used for Z positioning.

FIG. 10 shows data of Raman images acquired from tissues that were also imaged with AF/SHG and H&E (adjacent tissue). H&E images confirm the location of the ganglion cells and the AF/SHG images highlight those same regions that contain ganglion cells by the negative AF contrast. The Raman images are composed of 8-10 Raman images that are stitched together to form the final image of the tissue. Note that the entire Raman image took about 2 hours to acquire. This time-intensive Raman imaging is essential in this task for comprehensive analysis of the entire tissue. With these hyperspectral Raman images, users can extract the Raman spectrum from all parts of the tissue and compare the spectra of the ganglion cell regions to the spectra of other tissue regions. Hyperspectral Raman images are acquired for every sample that is imaged by H&E and AF/SHG and analysis performed of the hyperspectral Raman data.

Applying Multivariate Statistical Methods and Classification Algorithms to Determine Specificity of Raman Signals for Identifying Ganglion Cells There are multiple different approaches available to analyze hyperspectral Raman data and identify spectral differences. Analysis of spectral peak intensities that have statistically significant ($p<0.05$) differences for discriminating ganglion cells from adjacent tissue is a straightforward method. Principal component analysis (PCA), a multivariate statistical method, is also implemented in analyzing the Raman data. PCA is an unsupervised method for reducing data dimensionality and determining the combination of Raman spectral peaks that maximizes the data variance and group separation. PCA is a convenient, objective approach to determine whether the ganglion cells can be identified and discriminated from other tissue regions based on their Raman fingerprints. The PCA scatter plot in FIG. 10, which uses the first three principal components that capture the data variance, is a convenient way to visualize the degree with which the spectra obtained from the ganglion cell regions cluster together and how they separate from the spectra of adjacent tissue regions. The PCA plot indicates that the unique spectral signature of the ganglion cells can be used to discriminate the cells from the rest of the tissue.

For data classification, linear discriminant analysis (LDA) may also be used. LDA is a supervised modeling technique that finds the best linear combination of variables to discriminate between groups. As inputs for the LDA, the scores on the PCs which showed the highest discrimination of ganglion cells and adjacent tissues, are used. The classification sensitivity and specificity of this LDA model for correctly identifying ganglion cells is evaluated by using a leave-n-out cross validation method. Data is split into training and testing sets and the training sets are used to establish the LDA model. The test sets are used as inputs to the LDA model to determine diagnostic accuracy, classification sensitivity and specificity based on true negative, true positive, false negative and false positive values determined by the LDA model. For example, based on the PCA results shown in FIG. 10, when the three PCs were used as inputs into the LDA model and leave-n-out cross validation was performed, the classification sensitivity and specificity for identifying ganglion cells from adjacent tissue was 90% and 93% respectively. Measurements and analyses are performed on multiple tissue sections from different mice.

FIG. 1 is a graphical depiction of Raman peaks of ganglionic cells compared to those of adjacent non-ganglionic areas. FIG. 2 is a graphical illustration of a difference spectrum showing peaks that identify ganglion cells from non-ganglionic adjacent regions.

Figure 11:
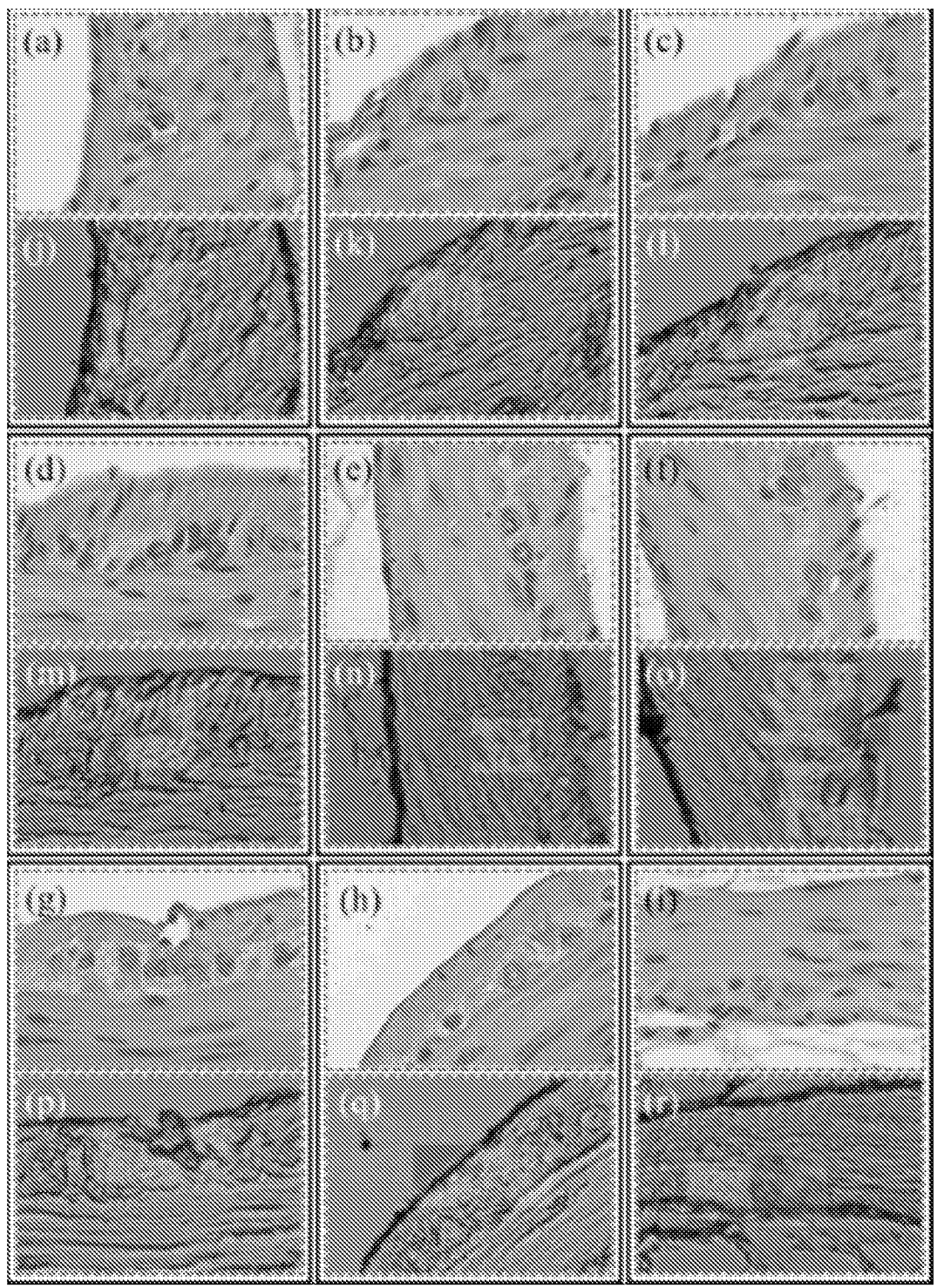
FIG. 11 shows an example of bright field stained H&E images (images (a)-(i)) and non-stained images overlaid with Raman imaging using the 1450 $cm^{-1}$ peak.
Figure 12:
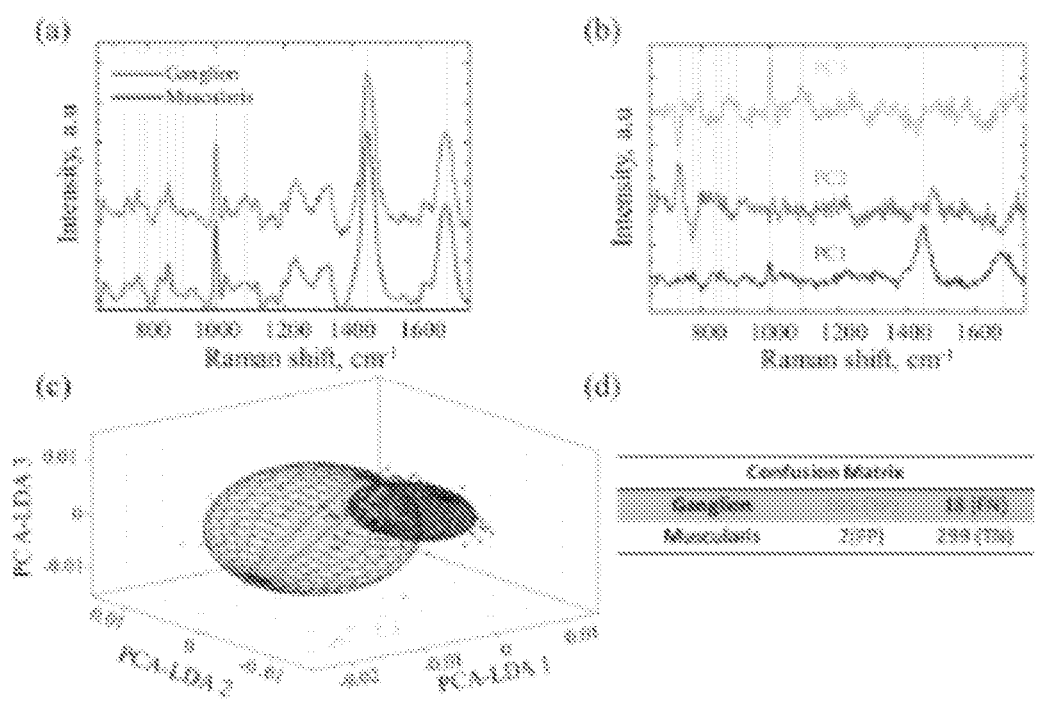
FIG. 12 shows an example of Raman signals (chart (a)) and principal components (chart (b)), covariance error ellipsoids (chart (c)), and a confusion matrix (d) determined from the Raman signals.

FIG. 11 depicts comparisons of stained tissue sections ((a)-(i)) and Raman signals ((j)-(r)) detected for various tissues. Raman signals (e.g., fingerprints) were extracted from 428 locations within ganglion cells (n=127) and muscle tissue (n=301) regions. FIG. 12 depicts a chart (a) of averaged Raman spectra for the 127 ganglion (upper line) and 301 muscle tissue (lower line) locations. FIG. 12 depicts a chart (b) of the first three principal components of the PCA analysis of the Raman signals, including Raman peaks that contributed most to discriminating the groups at 741, 770, 794, 837, 877, 901, 859, 1001, 1087, 1447, and 1676 $cm^{-1}$. The chart (b) demonstrates that ratio intensity between the 1447 and 1676 $cm^{-1}$ peaks is notable for the discrimination based on being assigned to lips and proteins. Spectra from ganglion cells had stronger peaks associated with nucleic acids (741, 794, 1087 $cm^{-1}$) and lips (770, 837, 877 $cm^{-1}$) than muscle tissue. FIG. 12 depicts a 3D plot (c) of covariance error ellipsoids with 90 percent interval confidence, which determines boundaries of the PCA-LDA prediction model. FIG. 12 depicts a confusion matrix (d) that quantifies the accuracy of the prediction model, 95 percent, with 86 percent sensitivity and 99 percent specificity, demonstrating the performance of the model (e.g., the use of SHG/AF signals to detect candidate regions and Raman signals to detect ganglion cells from the candidate regions) that can enable using the model for intraoperative ganglion tissue detection times.

Figure 13:
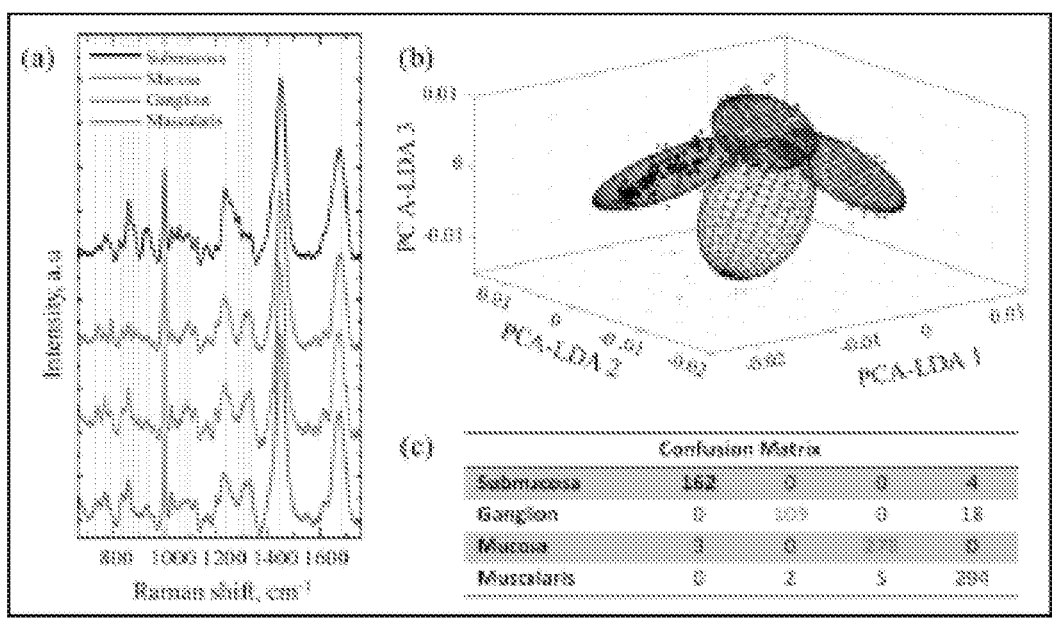
FIG. 13 shows an example of offset Raman average spectra (chart (a)), and a PCA-LDA plot of covariance error ellipsoids (chart (b)) and a confusion matrix (c) determined from the offset Raman average spectra.

FIG. 13 depicts a chart (a) (offset Raman average spectra) of Raman fingerprints of connective submucosa (n=166) and mucosa layers (n=281), showing the average Raman spectra of each group (e.g., submucosa top line, then mucosa, then ganglion, then muscularis). The submucosa demonstrated strong SHG signals due to the presence of collagen, and Raman peaks at 923, 938, 1056, 1235, 1286, 1309, and 1332 $cm^{-1}$ (e.g., peaks associated with collagen). FIG. 13 depicts a chart (b) (3D PCA-LDA plot with 90 percent interval confidence covariance error ellipsoids) and a confusion matrix (c) demonstrating discrimination of the four groups together, with an overall accuracy of 96 percent; each of the misclassified ganglion cell spectra were assigned to the muscularis group (e.g., the group having close proximity to the ganglion cells).

Blinded Experiments to Demonstrate Diagnosis of Normal and Non-Ganglionic Tissues After establishing the AF/SHG/Raman signals for ganglion cells, their accuracy in diagnosis based on optical signatures must be demonstrated. Tissues from wild type mice and knockout HD mice can be used. Experiments are blinded in which the final diagnosis, as determined by the H&E images, is not revealed to the researcher to avoid possible bias. Unstained and H&E stained adjacent tissue sections can be prepared for both wild type and knockout specimens. Using only the unlabeled specimens, AF/SHG imaging is performed first to determine if regions of interest that may contain ganglion cells are present. Hyperspectral Raman microscopy is then used to probe those specific regions and obtain the Raman spectra. After the hyperspectral Raman data is acquired from the tissue, the spectra is compared to the spectral database (i.e. the Raman 'gold standard' spectra) to determine if ganglion cells are present. Based on this result, the tissue type is classified as normal or non-ganglionic. The classification result is compared to the H&E diagnosis.

Figure 14:
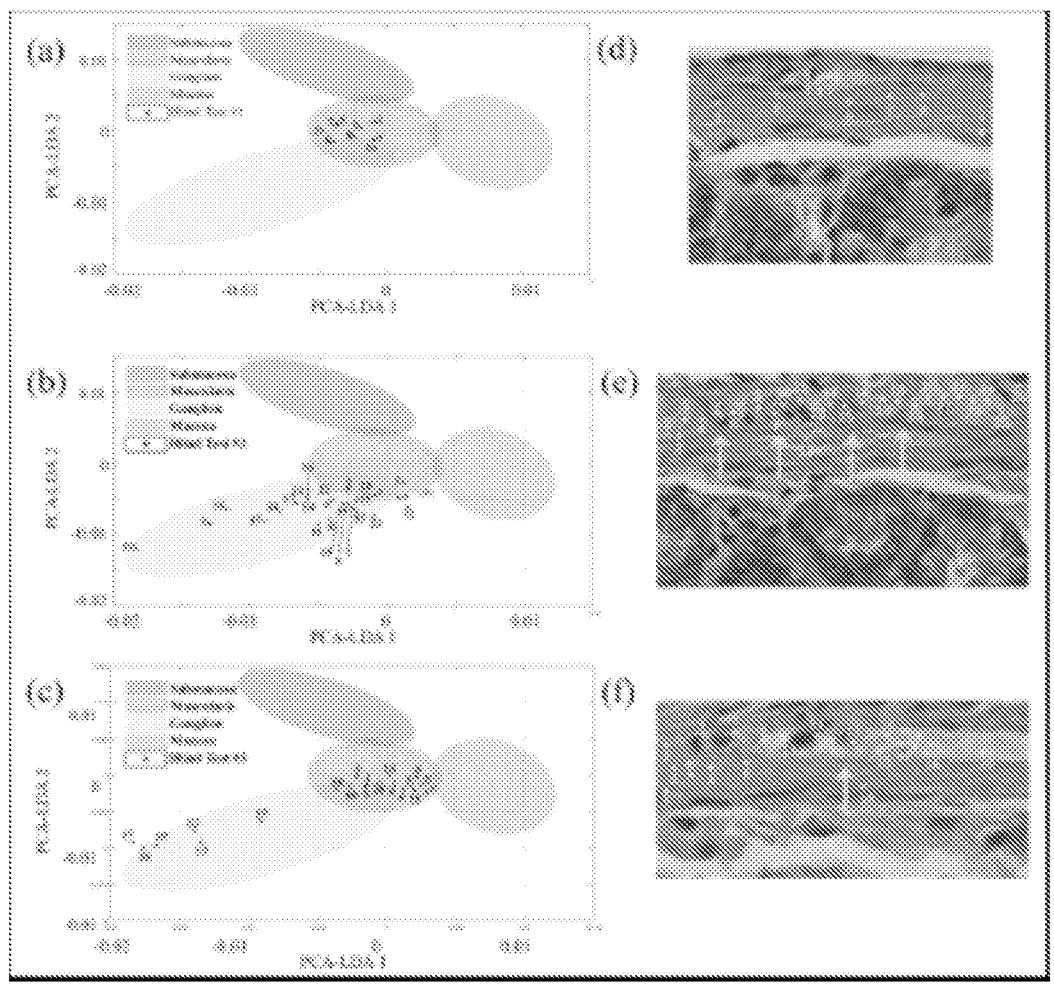
FIG. 14 shows a comparison of 2D PCA plots (charts (a)-(c)) and H&E images (images (d)-(f)).

For example, FIG. 14 depicts charts (a)-(c) (2D PCA plots showing classification of the Raman spectra from different tissue locations) and H&E images (d)-(f), demonstrating the accuracy of the model in detecting ganglion cells (including not detecting ganglion cells in some candidate regions identified by AF/SHG but in which ganglion cells were not present). In addition, to validate the use of SVM as a classification model, SVM was performed on the data from the blinded experiments with each Raman spectrum maintained as a 1340-dimensional vector that was classified and assigned to a group (e.g., using previous Raman data as a training set), and was found to have good agreement with the PCA-LDA classification model and the identification of cells from the H&E image analysis.

For classifying this Raman data, PCA, LDA, and leave-n-out cross validation that was used in signal gathering is not used here in an effort to avoid having the newly acquired spectra influence the classification algorithm. Rather, the classification model needs to be established based on the 'gold standard' database developed, and the unknown Raman spectra are classified as ganglion or non-ganglion based on this established model. To do this, support vector machine (SVM) classification is used, a machine learning supervised model that, when given a set of training examples (i.e. the gold standard database), builds a model that assigns new examples (i.e., the newly acquired data) to one category or the other. In SVM, a data point is viewed as a p-dimensional vector, and the goal is whether it is possible to separate such points into two groups with a (p-1)-dimensional hyperplane, making it a non-probabilistic binary linear classifier. The Raman image data can be processed based on averaging of signals from areas of two by two pixels (e.g., rather than from a single Raman image pixel), which can increase signal to noise ratio (SNR) and yield more reproducible data while retaining high spatial resolution.

In some embodiments, Matlab algorithms written incorporating a SVM classification method are used. The Raman spectral signatures from FIG. 10 were used as data points to develop the SVM model. Using this data as the 'gold standard' to define ganglion and non-ganglion spectra, the algorithm optimized the best hyperplane that represents the largest separation between the two classes: 'ganglion' and 'non-ganglion'. Next, unknown Raman spectra acquired from another tissue sample were acquired and compared to the classification results to H&E. Preliminary results indicated that SVM was able to classify 88% of spectra acquired in the negative contrast AF region (i.e. ganglion cells) as "ganglion cell". Meanwhile, 100% of spectra acquired in a negative contrast AF region that turned out to be non-ganglion cells in an H&E image was correctly classified as "non-ganglion". Optical excitation and emission parameters and AF, SHG, and Raman signatures that will accurately identify ganglion cells and distinguish them from adjacent tissue were established. The classification specificity and sensitivity of the spectra for identifying and discriminating ganglion cells and for identifying tissue type (normal, non-ganglionic) are also determined. Finally, classification models and algorithms are determined based on PCA, LDA, leave-n-out cross validation, and SVM. By using the SHG/AF imaging to detect candidate regions potentially having ganglion cells, and subsequently performing Raman imaging of the candidate regions, the ganglion cells can be detected accurately and rapidly (e.g., with the specificity enabled by the Raman imaging and targeted to a subset of regions—the candidate regions—using the SHG/AF imaging). Example 2: Demonstrating accurate diagnosis of normal and non-ganglionic tissue sections of intestinal biopsies from HD patients Establishing Optical Signatures of Ganglion Cells in Normal Intestinal Tissue Example 1 is designed to establish the methodology and classification methods for identifying ganglion cells. The optical signatures of murine specimens discovered in Example 1 can directly translate to human specimens, but are determined in Example 2. Samples of de-identified normal colonic tissue are obtained from the UC Davis Pathology Biorepository. The same serial sectioning of the tissue to obtain adjacent sections for H&E and label-free imaging is performed. The measurements and analyses described in Example 1 is performed on these normal human tissue sections. The outcome of Example 2 is determining if 1) the same spectral signatures of ganglion cells observed in Example 1 for murine tissue are also observed in human tissue or 2) if different spectral signatures of human ganglion cells are present that are still unique to identify the cells from adjacent tissue.

Determining the Diagnostic Accuracy of AF/SHG/Raman in Determining Aganglionosis, that is, in Establishing the Diagnosis of Hirschsprung Disease Once the optical signature of human ganglion cells is established, blinded analysis of samples from normal and non-ganglionic intestinal sections is performed. De-identified non-ganglionic tissue is obtained from the UC Davis Biorepository. Similar experiments as those described in Example 1 are performed on these specimens to determine if aganglionosis can be accurately diagnosed. To be sure of the tissue diagnosis, a clinical pathologist first evaluates the stained sections and only those samples that are "unequivocally Hirschsprung disease" and "unequivocally not Hirschsprung disease" are used. Other samples that are "insufficient" or "equivocal" are not used. Final diagnosis information is kept from the researcher until after the diagnosis is made based on the AF/SHG/Raman data. Sensitivity and specificity of multimodal optical imaging is calculated in comparison to the gold standard diagnosis. An effective sample size is needed to determine sensitivity and specificity of the presently disclosed techniques and methods. A power analysis was performed. With an estimated sensitivity of 97%, a precision of 0.07 (14% confidence interval), an alpha of 5%, and a prevalence of 30%, the sample size needed was 76. With an estimated specificity of 97%, a precision of 0.07, an alpha of 5%, and prevalence of 30%, the sample size needed was 33. Since both sensitivity and specificity need to be calculated, the total sample size needed is the larger of the two numbers, which is 76. Another power analysis was performed to determine the effective sample size needed to determine noninferiority between the presently disclosed imaging methods and conventional histopathology. With an estimated 80% power, a one-sided alpha of 5%, and allowing a 10% difference between the expected sensitivity of 97% and historical H&E specificity of 97%, the sample size needed is 72, with surgical sourcing of approximately 2-5 colonic biopsies per month. These include patients with known Hirschsprung disease, as well patients in whom Hirschsprung disease can be ruled out (and thus are normal controls). If 3 biopsies per month are performed, over a three year period more the 90 samples are more than enough to achieve proper power for statistical analysis. Results demonstrate that unique spectral signatures exist for ganglion cells in human tissue specimens that can be used to identify and discriminate them from adjacent tissue regions.

Example 3: Demonstrating Tissue Diagnosis on Unsectioned, Whole Tissue Patient Biopsies SHG/AF/Raman System for Fully Automated Analysis of Whole Tissue Biopsies Examples 1-2 utilize two separate, manual optical systems, a multiphoton AF/SHG microscope and a hyperspectral Raman microscope. The measurements are also made on tissue sections. Example 3 demonstrates fully automated analysis and diagnosis of unsectioned, whole tissue patient biopsies, i.e., the final clinical implementation of the systems and methods: a single, combined system for automated tissue analysis. Existing SHG/AF microscopes are modified to add on the hyperspectral Raman capability and implement full automation. In some embodiments of the system, a microscope has an additional entrance port that allows for the Raman excitation laser to be coupled into the system. In further embodiments, an additional exit port is also available and used to collect the Raman scattered photons. For full automation, motorized mirrors (Newport), optical shutters (Thorlabs), and a positioning stage (Physik Instruments), can be added to the system. In some embodiments of the system, a National Instruments (NI) board and LabView software can be used for hardware control and data acquisition. All other components of the hyperspectral Raman microscope described in Example 1 are duplicated in this setup. The LabView software controls all aspects of hardware automation, such as switching between the multiphoton and the CW Raman laser, triggering the detectors for acquiring the optical signals, generating the images based on the acquired signals, scanning the stage for image mosaicking, and changing the z-plane focus. The Labview software also has the function to call the Matlab software for performing the image processing, analysis, and classification as described in Example 1.

Automated Image Acquisition, Spectral Analysis, and Tissue Classification

After the user places an unsectioned piece of tissue on the microscope, the microscope is able to automatically i) generate an AF/SHG image; ii) pinpoint regions for further hyperspectral Raman analysis; iii) acquire hyperspectral Raman data from those regions; iv) optically section the tissue and repeat the measurement and analysis on another z-plane of the tissue; v) compare spectra to a gold standard spectral database and arrive at a final diagnosis.

After the tissue is mounted on the microscope stage, the stage can move to the z-plane of the tissue closest to the glass coverslip. To calibrate the optical system on the tissue orientation, the software scans the stage to find the tissue edge based on a brightfield intensity threshold difference between the tissue and the coverslip. Starting from this edge, an AF/SHG image is acquired. Detection of the SHG signal also assists in providing information to the system on the location of the muscle layers. The stage moves to the next position and another image is acquired. This process can be repeated and the images mosaicked by the software to create a larger field of view image. Once the image is created, it is exported to the Matlab software, which runs a program that automates the detection of regions of interest that possibly contain ganglion cells (i.e. the program detects the negative contrast dark regions based on a low signal intensity threshold criteria). The pixel coordinates of these regions are fed back to the Labview software, which moves the stage to those coordinates. The system can switch to the hyperspectral Raman mode and Raman data is collected from these regions. The spectral data is then fed to a Matlab routine that processes and classifies the data by comparing to reference spectra using SVM. The stage is then stepped in the longitudinal Z-axis in increments defined by the user (e.g. 5 μm step size) and the process can be repeated. A final diagnosis of the tissue type (normal, non-ganglionic) is determined. The tissue can then processed by H&E and diagnosed by a pathologist, and the two diagnoses can be compared.

Determining Maximum Tissue Depth that can be Analyzed with AF/SHG/Raman

The system is designed to image up to 400 μms. Automated image acquisition can be performed with Z-axis scanning in increments of 20 μms to determine the maximum depth at which optical signals can no longer be detected for generating images. It is known that multiphoton microscopy can typically image several hundreds of microns deep into tissue due to the intrinsic confocality and use of long wavelengths that can penetrate deep into tissue. For hyperspectral Raman imaging, however, because excitation can be performed at 785 nm, the tissue penetration depth at that wavelength may not allow such deep probing. Thus, different excitation wavelengths from about 700 through about 1600 nm can be tested using a tunable CW laser. At longer wavelengths (1064-1600 nm), optical filters in the hyperspectral Raman beam path of the system and the detector may be need to be changed. In some embodiments, the detector may be changed to an InGaAs CCD camera capable of sensitivity at longer wavelengths.

In some embodiments, imaging an about 2 mm×2 mm image plane can be performed in approximately 50 seconds. Analysis of an initial 15 sections is therefore expected to take about 10 minutes to about 20 minutes, which is faster than current methods. Currently, if pathologists see ganglion cells in this pilot section, no further analysis is needed. If needed, additional analysis of sections beyond the first 15 sections would add approximately 1 minute/section to the total time.

Equivalents

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

Unless otherwise defined, all technical and scientific terms used herein have the same meaning as commonly understood by one of ordinary skill in the art to which this disclosure belongs. All nucleotide sequences provided herein are presented in the 5' to 3' direction.

The embodiments illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure.

Thus, it should be understood that although the present disclosure has been specifically disclosed by specific embodiments and optional features, modification, improvement and variation of the embodiments therein herein disclosed may be resorted to by those skilled in the art, and that such modifications, improvements and variations are considered to be within the scope of this disclosure. The materials, methods, and examples provided here are representative of particular embodiments, are exemplary, and are not intended as limitations on the scope of the disclosure.

The scope of the disclosure has been described broadly and generically herein. Each of the narrower species and subgeneric groupings falling within the generic disclosure also form part of the disclosure. This includes the generic description with a proviso or negative limitation removing any subject matter from the genus, regardless of whether or not the excised material is specifically recited herein.

In addition, where features or aspects of the disclosure are described in terms of Markush groups, those skilled in the art will recognize that embodiments of the disclosure may also thereby be described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. A method for determining if a tissue is ganglionic or non-ganglionic comprising:
   a) identifying a region of interest in a tissue suspected to contain ganglion cells by at least one of autofluorescence (AF) or Second Harmonic generation (SHG) imaging of the tissue;
   b) generating at least one hyperspectral Raman image of a tissue from the region of interest; and
   c) identifying the tissue as ganglionic or non-ganglionic by comparing a Raman signature intensity from the hyperspectral Raman image of the region of interest to a respective Raman signature of an adjacent tissue, wherein the Raman signature comprises at least one of 710 cm$^{-1}$±1 cm$^{-1}$, 734 cm$^{-1}$±1 cm$^{-1}$, 797 cm$^{-1}$±1 cm$^{-1}$, 859 cm$^{-1}$±1 cm$^{-1}$, 924 cm$^{-1}$±1 cm$^{-1}$ 1216 cm$^{-1}$±1 cm$^{-1}$, 1362 cm$^{-1}$±1 cm$^{-1}$, 1440 cm$^{-1}$±1 cm$^{-1}$, or 1660 cm$^{-1=1}$ cm$^{-1}$ and an intensity peak determines ganglionic tissue from a non-ganglionic tissue.

2. The method of claim 1, wherein analyzing the image further comprises evaluating Raman signatures for peaks at about 741 cm$^{-1}$, 770 cm$^{-1}$, 794 cm$^{-1}$, 837 cm$^{-1}$, 877 cm$^{-1}$, 901 cm$^{-1}$, 859 cm$^{-1}$, 1001 cm$^{-1}$, 1087 cm$^{-1}$, 1447 cm$^{-1}$, or 1676 cm$^{-1}$.

3. The method of claim 2, wherein analyzing the image further comprises evaluating a ratio of Raman peaks at about 1447 cm$^{-1}$ and about 1676 cm$^{-1}$.

4. The method of claim 1, wherein analyzing the image comprises evaluating Raman signatures for peaks associated with at least one of a lipid, a protein, or a collagen.

5. The method of claim 1, wherein the region of interest is identified as a region of lower autofluorescence relative to the adjacent tissue.

6. The method of claim 1, wherein autofluorescence is tuned to different excitation wavelengths between about 750 nm to about 1050 nm.

7. The method of claim 1, comprising performing the SHG by:
   tuning a laser to a wavelength from about 700 nm to about 1600 nm;
   centering a bandpass filter from about 350 nm to about 800 nm; and
   collecting a SHG signal using the centered bandpass filter.

8. The method of claim 1, wherein hyperspectral Raman imaging is tuned to excitation wavelengths between about 785 nm to about 1085 nm using a tunable CW laser.

9. The method of claim 1, wherein more than one hyperspectral Raman image is mosaicked, using at least one of a line scan microscope or a point scan microscope, to generate a multidimensional Raman image of the tissue.

10. The method of claim 1, further comprising generating Brightfield images of the tissue from the region of interest and comparing the images to the one or more of AF, SHG, or Raman images.

11. The method of claim 1, wherein tissue from the region of interest is further compared to tissue sample analyses performed using Haemotoxylin and Eosin (H&E) staining or calretinin immunohistochemistry to verify whether the region of interest tissues are normal or non-ganglionic.

12. The method of claim 1, wherein the method is used to diagnose Hirschsprung disease.

13. The method of claim 1, wherein identifying the tissue as ganglionic comprises determining that the intensity peak of the Raman signature intensity from the hyperspectral Raman image of the region of interest is lower than an intensity peak of the respective Raman signature of the adjacent tissue.

14. A method of detecting ganglion cells from a tissue of a subject, comprising:
   evaluating the tissue using at least one of second harmonic generation or autofluorescence to detect at least one candidate region potentially having ganglion cells; and
   evaluating the at least one candidate region relative to a region of the tissue adjacent to the at least one candidate region using Raman spectroscopy to determine whether the at least one candidate region has a ganglion cell;
   wherein the evaluating using autofluorescence comprises detecting the at least one candidate region as a region of lower autofluorescence relative to the tissue adjacent to the at least one candidate region.

15. The method of claim 14, wherein evaluating the at least one candidate region using Raman spectroscopy comprises applying, as input to at least one of a principle component analysis model, a linear discriminant analysis model, or a support vector machine model, one or more Raman peaks having values of about 741 cm-1, 770 cm-1, 794 cm-1, 837 cm-1, 877 cm-1, 901 cm-1, 859 cm-1, 1001 cm-1, 1087 cm-1, 1447 cm-1, or 1676 cm-1.

16. The method of claim 14, further comprising diagnosing a Hirschsprung disease based at least on determining that the at least one candidate region has the ganglion cell.

* * * * *